US010421770B2

(12) United States Patent
Liu

(10) Patent No.: US 10,421,770 B2
(45) Date of Patent: Sep. 24, 2019

(54) PHARMACEUTICAL COMPOSITION OF CARBOPLATIN BASED CO-CRYSTALS AND USE THEREOF

(71) Applicant: SYN-NAT PRODUCTS ENTERPRISE LLC, Edison, NJ (US)

(72) Inventor: Xiaozhong Liu, Potomac, MD (US)

(73) Assignee: SYN-NAT PRODUCTS ENTERPRISE LLC, Edison, NJ (US)

( * ) Notice: Subject to any disclaimer, the term of this patent is extended or adjusted under 35 U.S.C. 154(b) by 0 days.

(21) Appl. No.: 15/736,178

(22) PCT Filed: Jun. 20, 2016

(86) PCT No.: PCT/US2016/038340
§ 371 (c)(1),
(2) Date: Dec. 13, 2017

(87) PCT Pub. No.: WO2016/205785
PCT Pub. Date: Dec. 22, 2016

(65) Prior Publication Data
US 2018/0179240 A1 Jun. 28, 2018

Related U.S. Application Data

(60) Provisional application No. 62/182,142, filed on Jun. 19, 2015.

(51) Int. Cl.
*C07F 15/00* (2006.01)
*C07D 207/267* (2006.01)
*A61P 35/00* (2006.01)
*A61K 31/282* (2006.01)
*A61K 45/06* (2006.01)

(52) U.S. Cl.
CPC ........ *C07F 15/0093* (2013.01); *A61K 31/282* (2013.01); *A61K 45/06* (2013.01); *A61P 35/00* (2018.01); *C07D 207/267* (2013.01); *C07B 2200/13* (2013.01)

(58) Field of Classification Search
CPC ...... C07F 15/0093; A61P 35/00; A61K 45/06; A61K 31/282; C07D 207/267; C07B 2200/13
See application file for complete search history.

(56) References Cited

U.S. PATENT DOCUMENTS

| 5,922,689 | A  | 7/1999  | Shaw           |
|-----------|----|---------|----------------|
| 6,297,245 | B1 | 10/2001 | Shaw           |
| 6,340,770 | B1 | 1/2002  | Kwon et al.    |
| 6,699,901 | B1 | 3/2004  | Yang et al.    |
| 7,927,613 | B2 | 4/2011  | Almarsson et al.|
| 8,247,445 | B2 | 8/2012  | Kay et al.     |
| 9,447,130 | B1 | 9/2016  | Liu et al.     |
| 2003/0103896 | A1 | 6/2003 | Smith         |
| 2005/0165093 | A1 | 7/2005 | Wang et al.    |
| 2007/0197517 | A1 | 8/2007 | Jani et al.    |
| 2008/0063642 | A1 | 3/2008 | Adelman et al. |
| 2008/0161251 | A1 | 7/2008 | Curry et al.   |
| 2009/0281319 | A1 | 11/2009| Du Preez       |
| 2010/0068178 | A1 | 3/2010 | Gokaraju et al.|
| 2011/0287110 | A1 | 11/2011| Dewhirst et al.|
| 2014/0255394 | A1 | 9/2014 | Hoeschele et al.|
| 2018/0085377 | A1 | 3/2018 | Liu            |
| 2018/0169055 | A1 | 6/2018 | Liu            |
| 2018/0186822 | A1 | 7/2018 | Liu            |
| 2018/0289662 | A1 | 10/2018| Liu            |

FOREIGN PATENT DOCUMENTS

| CN | 104127402 A     | 11/2014 |
|----|-----------------|---------|
| EP | 1 473 298 A1    | 11/2004 |
| EP | 2 743 252 A1    | 6/2014  |
| WO | WO 2004/099224 A1 | 11/2004 |
| WO | WO 2011/029415 A1 | 3/2011  |
| WO | WO 2015/058067 A1 | 4/2015  |
| WO | WO 2016/172393 A1 | 10/2016 |
| WO | WO 2016/187191 A1 | 11/2016 |
| WO | WO 2016/205782 A1 | 12/2016 |
| WO | WO 2016/205785 A1 | 12/2016 |
| WO | WO 2016/210418 A1 | 12/2016 |

OTHER PUBLICATIONS

Duggirala, N.K. "Pharmaceutical cocrystals: along the path to improved medicines." Chemical Communications 52.4 (2016): 640-655.*
Galek, P.T.A., "One in half a million: a solid form informatics study of a pharmaceutical crystal structure." CrystEngComm 14.7 (2012): 2391-2403.*
Li, GQ et al., "Effect of Dicyclopatin, a Novel Platinum Chemotherapeutical Drug, on Inhibiting Cell Growth and Inducing Cell Apoptosis," PLOS One, 7(11):e48394 (2012).
Omar, E.K. et al., "Does the Key to Treat Rheumatoid Nodules Lie with Oncology?—Is Cisplatin an Option?," BioMed Central Musculoskeletal Disorders, 14 (Suppl. 1): A5, BioMed Central (2013).
Kreiner, B. et al., "Neuroendocrine Carcinoma of the Seminal Vesicles Presenting with Lambert Eaton Syndrome: a Case Report," Journal of Medical Case Reports, 4:320, p. 1-4, BioMed Central (2010).
Li, S. et al., "Phase I Clinical Trial of the Novel Platin Complex Dicycloplatin: Clinical and Pharmacokinetic Results," Int'l Journal of Clinical Pharmacology and Therapeutics, vol. 51, No. 2, pp. 96-105 (2013).
Liu, KJ et al., "A Double-Blind, Randomized Phase II Study of Dicycloplatin Plus Paclitaxel Versus Carboplatin Plus Paclitaxel as First-Line Therapy for Patients with Advanced Non-Small-Cell Lung Cancers," Arch Med Sci, 10, 4: 717-724, Elsevier, Netherlands (2014).

(Continued)

Primary Examiner — John M Mauro
(74) Attorney, Agent, or Firm — Nixon & Vanderhye P.C.

(57) ABSTRACT

The current invention relates to series of co-crystals of carboplatin with cyclic amides as co-formers and their pharmaceutical use. The co-crystals of the current invention may be used in the treatment or prevention of cancers.

18 Claims, 10 Drawing Sheets

(56) References Cited

OTHER PUBLICATIONS

Yang, X. et al., "Determination Methods for the Anticancer Drug Dicycloplatin, a Supramolecule Assembled Through Hydrogen Bonding", Analyst, 140:2704-2712, The Royal Society of Chemistry (2015).
International Search Report of PCT/US2016/028720 dated Jul. 15, 2016, issued by the International Bureau.
International Search Report of PCT/US2016/032856 dated Aug. 16, 2016, issued by the International Bureau.
International Search Report of PCT/US2016/038333 dated Sep. 28, 2016, issued by the International Bureau.
International Search Report of PCT/US2016/038340 dated Sep. 13, 2016, issued by the International Bureau.
International Search Report of PCT/US2016/039572 dated Sep. 23, 2016, issued by the International Bureau.
European Search Report of EP 16 81 2609 dated Oct. 16, 2018, issued by the European Patent Office.
Notice of Allowance dated May 7, 2019 in U.S. Appl. No. 15/736,179, 371(c) dated Dec. 13, 2017.
Amendment and Reply to Office Action submitted Jan. 7, 2019 in U.S. Appl. No. 15/736,179, 371(c) dated Dec. 13, 2017.
Office Action dated Oct. 5, 2018 in U.S. Appl. No. 15/736,179, 371(c) dated Dec. 13, 2017.
Yu, J. J. et al., "Dicycloplatin, a Novel Platinum Analog in Chemotherapy: Synthesis of Chinese Pre-clinical and Clinical Profile and Emerging Mechanistic Studies," Anticancer Research 34:455-464 (2014), Highwire Press.

* cited by examiner

| HV | WD | mag | mode | HFW | dwell | det | ——— 100 μm ——— |
|---|---|---|---|---|---|---|---|
| 10.0kV | 5.4mm | 500x | SE | 480μm | 6μs | ETD | Nova Nano SEM230 |

| HV | WD | mag | mode | HFW | dwell | det | ——— 10 μm ——— |
|---|---|---|---|---|---|---|---|
| 10.0kV | 5.4mm | 5000x | SE | 48.0μm | 6μs | TLD | Nova Nano SEM230 |

| HV | WD | mag | mode | HFW | dwell | det | ——— 3 μm ——— |
|---|---|---|---|---|---|---|---|
| 10.0kV | 5.4mm | 20,000x | SE | 12.0μm | 6μs | TLD | Nova Nano SEM230 |

PHARMACEUTICAL COMPOSITION OF CARBOPLATIN BASED CO-CRYSTALS AND USE THEREOF

FIELD OF THE INVENTION

The current invention relates to a series of co-crystals of carboplatin with cyclic amides and the pharmaceutical use of these co-crystals. The co-crystals of the current invention may be used in the treatment or prevention of various diseases such as cancer. The current invention also relates to the processes to produce such co-crystals.

BACKGROUND OF THE INVENTION

Pharmaceutical co-crystallization has attracted great amount of academic, industrial and therapeutic interests by co-crystallization of two or more pure compounds with crystal engineering to create a new functional material. Specifically, pharmaceutical co-crystals are defined as "co-crystals in which the target molecule or ion is an active pharmaceutical ingredient, API, and it bonds to the co-crystal former(s) through hydrogen bonds." Almarsson M. and Zaworotko J., *Chem. Commun.*, 2004: 1889. Pharmaceutical co-crystals are nonionic supramolecular complexes and can be used to improve physiochemical properties such as solubility, stability and bioavailability in pharmaceutical development without changing the chemical composition of the active pharmaceutical ingredient (API).

Carboplatin, one of the second-generation antitumor drugs of platin analogues, has received worldwide approval and use due to its lower toxicity in comparison to cisplatin. Unfortunately, although to a milder degree compared to first generation platins, carboplatin still results in a number of side effects, such as myelosuppression. In addition, carboplatin may be used only for a limited spectrum of cancers. Therefore, the search continues for orally active carboplatin analog compounds that are less toxic, cause less drug-resistance and provide more versatility.

Consequently, it is desirable to improve the physiochemical and therapeutic properties of cisplatin, carboplatin and other platin with co-crystallization technology. In some cases, there is no need to change the basic structure of the platin as the API, while properties such as solubility, stability, permeability and bioavailability can be improved. For example, it would be possible to significantly enhance the bioavailabiltiy of a platin API with co-crystallization, so that the co-crystal can be therapeutically effective in certain environment of use and maintain the level for a prolonged period of time.

The present invention provides a series of co-crystals of carboplatin, where one of the co-crystal formers is a cyclic amide. The co-crystals of this invention may satisfy one or more of the targeted objectives, such as but not limited to increased solubility, stability and bioavailability and more versatility in pharmaceutical use.

SUMMARY OF THE INVENTION

The present invention provides a series of co-crystals each comprising a carboplatin (CBP) and a cyclic amide as a co-former, and methods of making and using the same.

In some embodiments, the cyclic amide co-former is selected from CF-01 to CF-14 in Table 1, wherein R represents a hydrogen, a halogen, an amino group, a C1-C6 alkyl group, a C3-C6 cycloalkyl group, a cyanide group, a hydroxyl group, an acyl group, a phosphoryl group, a phosphoroamido group, a hydroxylcarboxyl group, a phenyl group, or an aliphatic group.

TABLE 1

Cyclic amides as co-crystal formers for the platin-based co-crystals

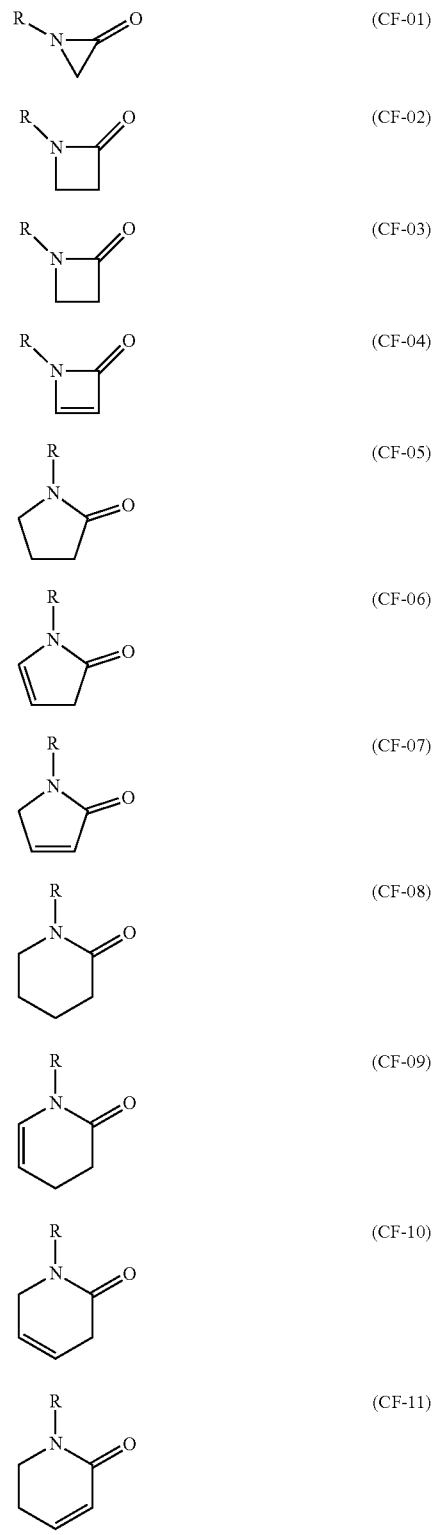

TABLE 1-continued

Cyclic amides as co-crystal formers for the platin-based co-crystals

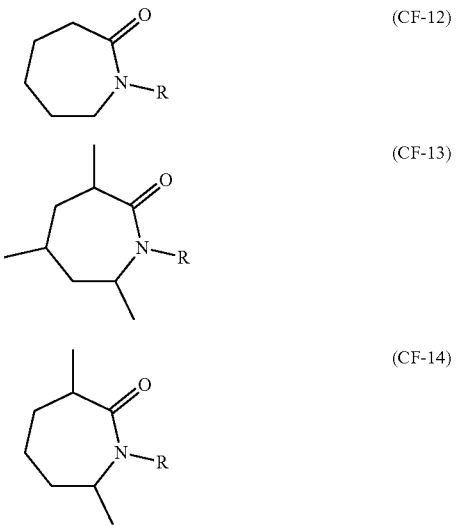

In some embodiments, the co-crystal comprises carboplatin and CF-05 from Table 1; and in one particular embodiment, R is a methyl group. Specifically, the co-crystal of the current invention may comprise carboplatin and N-methyl-2-pyrrolidone (NMP), which are bonded at a 1:1 ratio. Such a co-crystal is termed CBP-NMP. In some embodiments, the CBP-NMP co-crystal of the present invention may have an x-ray diffraction pattern comprising peaks at diffraction angles 2-Theta of 16.0° and 24.5°±0.2 as said peaks are set forth in FIG. 10.

In one aspect, the co-crystal of the present invention is formed where carboplatin, the active pharmaceutical ingredient (API), and cyclic amide, the co-crystal former, are bonded together through hydrogen bonds. In some embodiments, other non-covalent interactions may also be in the co-crystal. In some embodiments, other non-covalent and covalent interactions may also be present in the co-crystal.

In another aspect, the present invention provides a pharmaceutical composition comprising a compound of the co-crystal comprising carboplatin and a co-former cyclic amide. In some embodiments of the pharmaceutical composition, the carboplatin is the API.

One aspect of the invention relates to carboplatin-based co-crystals which provide a sufficient level of bioavailability to be therapeutically effective in pharmaceutical use and maintains the level for a therapeutically effective period of time.

Another aspect of the invention is to provide uses of carboplatin-based co-crystals (e.g. the co-crystals of Formal I) in certain indications; in some embodiments the uses of the co-crystals extend beyond the uses of carboplatin by itself. In some embodiments, the present invention relates to treating or preventing a disease in a subject in need thereof comprising administering to the subject the pharmaceutical composition comprising the co-crystal of Formula I, wherein the co-crystal is in a therapeutically effective amount. In some embodiments, the disease is a cancer; in other embodiments, the disease is a virus infection.

In one aspect, the present invention involves the use of a pharmaceutical composition comprising a compound of the co-crystal of the current invention to kill a malignant cell in a subject suffering from cancer by contacting the malignant cell with an effective amount of the co-crystal.

In one aspect, the present invention concerns the use of pharmaceutical compositions comprising a compound of one of the co-crystals of the current inventions to treat cancer cells with an effective amount of the compound alone or in combination with at least one therapeutic agent or adjuvant therapy agent. The target cancers include, but are not limited to prostate cancer, colorectal cancer, renal adenocarcinoma and leucocythemia.

In some embodiments of the treatment of cancers, the therapeutically effective amount of the compound is about 0.01 to about 10 mg/kg body weight, and in some particular embodiments about 0.01 to about 5 mg/kg body weight.

In some embodiments of treatment of virus diseases, the therapeutically effective amount of the compound is about 0.01 to about 10 mg/kg body weight, and in some particular embodiments about 0.01 to 5 mg/kg body weight.

DETAILED DESCRIPTION OF THE INVENTION

Figure 1:
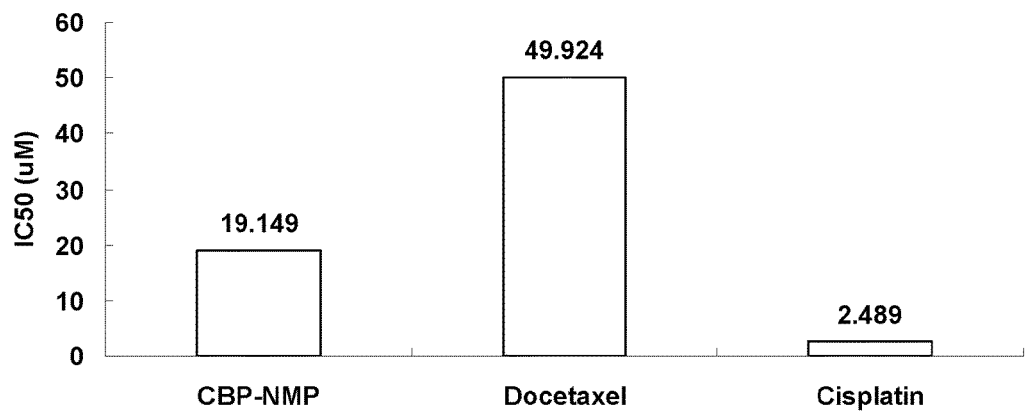
FIG. 1 shows the $IC_{50}$ values of CBP-NMP and the control chemicals docetaxel and cisplatin in PC-3 prostate cancer cell line.

The following description of certain embodiment(s) is merely exemplary in nature and is in no way intended to limit the invention, its application, or uses. As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless defined otherwise, all technical and scientific terms used herein have the same meaning as is commonly understood by one of skill in the art to which this invention belongs. All patents and publications referred to herein are incorporated by reference in their entireties.

The term "effective amount" or "therapeutically effective amount" refers to that amount of a compound or combination of compounds as described herein that is sufficient to effect the intended application including, but not limited to, prophylaxis or treatment of diseases. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells and/or tissues (e.g., the reduction of cell proliferation and/or morphological alteration of the tissue). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A "prophylactic effect" (e.g. terms such as "prophylaxis," "prevent" and "reducing the likelihood for developing") includes delaying or eliminating the appearance of a disease or condition, delaying or eliminating the onset of symptoms of a disease or condition, slowing, halting, or reversing the progression of a disease or condition, or any combination thereof by administering a drug before the onset of the disease or condition. A "treatment effect" (e.g. with terms such as "treatment" and "treat") includes reducing or eliminating the appearance of a disease or condition, reducing or eliminating the symptoms of a disease or condition, slowing, halting, or reversing the progression of a disease or condition, or any combination thereof by administering a drug after the onset of the disease or condition.

A "subject" as the term is used herein, refers to a human or non-human animal. In some embodiments, the subject is a mammal. In some embodiments, the subject is human.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. In some embodiments, the variation is from 0% to 15%; in some particular embodiments from 0% to 10%; and in other embodiments from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds used in the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Compound of the co-crystal" refers to crystalline and amorphous forms made from the co-crystal, wherein "made from" means left unaltered or processed with known methods such as but not limited to dissolving, condensing, crystalline disruption, drying, grinding, compaction, and polymer film coating. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The present invention relates to a co-crystal comprising a carboplatin (CBP) and a cyclic amide. In some embodiments, the co-crystals of the present invention have the structure of Formula (I):

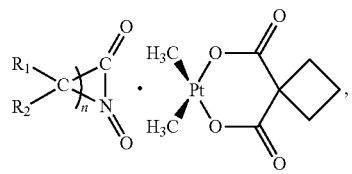

Formula I wherein n is an integer selected from 1-12, and when n≥2, the carbon atoms on the cyclic amide are connected by single or double bonds; wherein $R_1$, $R_2$ and $R_3$ are the same as or different from one another, and each independently represents a hydrogen, a halogen, an amino group, a C1-C6 alkyl group, a C3-C6 cycloalkyl group, a cyanide group, a hydroxyl group, an acyl group, a phosphoryl group, a phosphoroamido group, a hydroxylcarboxyl group, a phenyl group, or an aliphatic group.

In some embodiments, n is 2, 3, 4, or 5. In some embodiments, each of R1, R2 and R3 independently represents any one of hydrogen, methyl, vinyl, isopropyl, hydroxylmethyl, cyclohexanemethyl, cyanomethyl, and aminomethyl groups.

In some embodiments, n is 3 and the carbon atoms on the cyclic amide are connected by single bonds. In one particular embodiment, n is 3, the carbon atoms on the cyclic amide are connected by single bonds, and R3 represents any one of methyl, vinyl, isopropyl, hydroxylmethyl, cyclohexanemethyl, cyanomethyl, and aminomethyl groups.

In some embodiments, the cyclic amide co-former may be selected from the following structures:

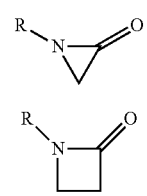

(CF-01)

(CF-02)

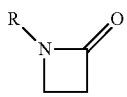 (CF-03)

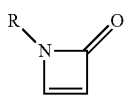 (CF-04)

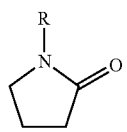 (CF-05)

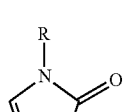 (CF-06)

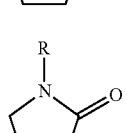 (CF-07)

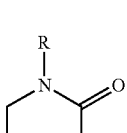 (CF-08)

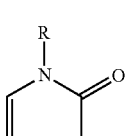 (CF-09)

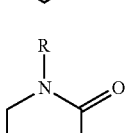 (CF-10)

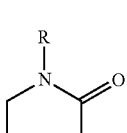 (CF-11)

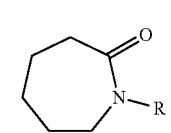 (CF-12)

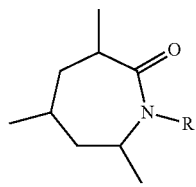 (CF-13)

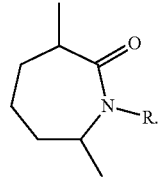 (CF-14)

wherein R represents a hydrogen, a halogen, an amino group, a C1-C6 alkyl group, a C3-C6 cycloalkyl group, a cyanide group, a hydroxyl group, an acyl group, a phosphoryl group, a phosphoroamido group, a hydroxylcarboxyl group, a phenyl group, or an aliphatic group.

Figure 10:
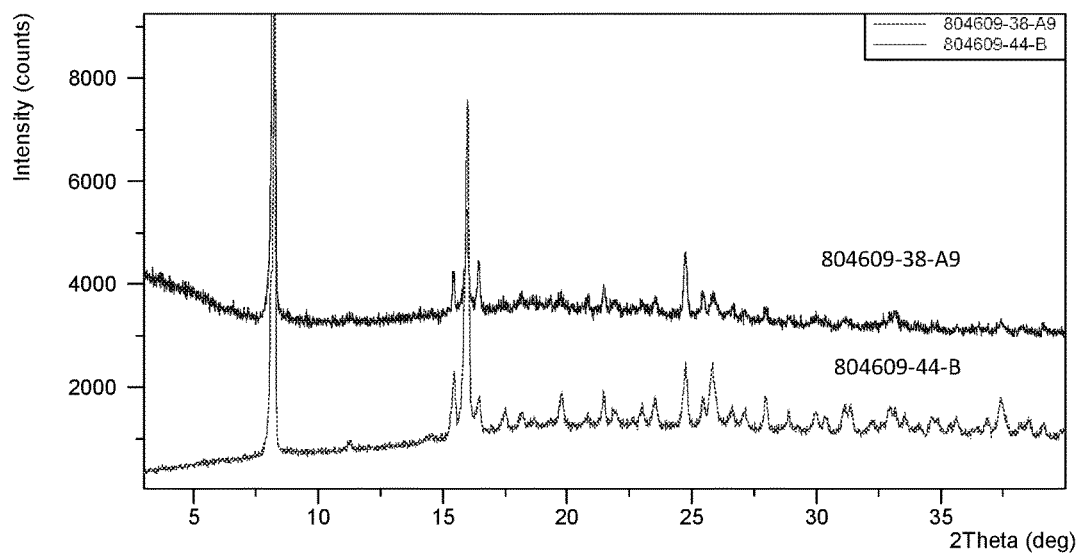
FIG. 10 shows the XRPD pattern of a CBP-NMP sample from different mixtures.

In some embodiments, the co-crystal comprises CBP and N-methyl-2-pyrrolidone (NMP) bonded at a 1:1 ratio. Such co-crystal may be termed CBP-NMP. In some embodiments, the co-crystal has an x-ray diffraction pattern comprising peaks at diffraction angles 2-Theta of 16.0° and 24.5°±0.2. In some embodiments, the co-crystal has an x-ray diffraction pattern comprising peaks at diffraction angles 2-Theta of 16.0° and 24.5°±0.1. In some embodiments, the co-crystal has an x-ray diffraction pattern comprising peaks at diffraction angles 2-Theta of 16.0° and 24.5°±0.05. In some embodiments, the co-crystal has an x-ray diffraction pattern comprising peaks as set forth in FIG. 10. In some embodiments, the co-crystal has an x-ray diffraction pattern substantially similar to the pattern as set forth in FIG. 10.

In some embodiments, the co-crystal comprising CBP and NMP may have a structure of Formula II:

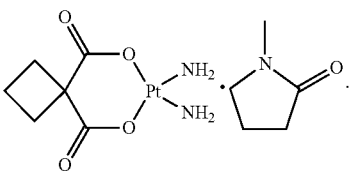

Formula II

In some embodiments, the co-crystal of the present invention comprises: (i) a cyclic amide as a co-former; and (ii) carboplatin as a co-former and the active pharmaceutical ingredient (API). In some embodiments, carboplatin and the cyclic amide are bonded in 1:1 ratio.

As described here, the solid state of the co-crystal of the current invention is any crystalline polymorphic forms or a mixture thereof. The co-crystal may also be made into an amorphous form, which may be combined with any crystalline forms. In some embodiments, the solid state of the co-crystal of the current invention is Form A, as shown in the X-ray powder diffraction pattern (XRPD) of FIG. 10 for sample 804609-44-B. Form A of the co-crystal of CBP-NMP in this invention was also confirmed by single crystal characterization and other determination methods. In other embodiments, the solid state of the co-crystal is an amorphous form. Different forms of the co-crystal of the current invention may be obtained through different crystallization process and the co-crystals may be made into amorphous forms with known technology.

The co-crystals of the current invention (e.g. co-crystal formed by CBP and cyclic amide of Table 1) demonstrate a sufficient level of bioavailablity to be therapeutically effective in pharmaceutical use and maintains that level in a subject for a prolonged period of time.

The co-crystals of the current invention (e.g. CBP-NMP) may be produced by a process comprising: (i) providing and mixing carboplatin, cyclic amides and an appropriate solvent, (ii) slurrying or stirring the mixture from step i) for a sufficient period of time; and (iii) isolating the co-crystal formed thereby.

The specific conditions of the process may be adjusted to ensure optimized purity, quantity, and/or physiochemical properties. In some embodiments, the proper ratio is in the molar range of 1:0.1-1:20, 1:0.2-1:20, 1:0.3-1:20, 1:0.4-1:20, 1:0.5-1:20, 1:0.6-1:20, 1:0.7-1:20; 1:0.8-1:20, 1:0.9-1:20, 1:1-1:1.20, 1:2-1:20, 1:3-1:20, 1:4-1:20, 1:5-1:20, 1:6-1:18, 1:7-1:15, 1:8-1:13, 1:9-1:12, or 1:10-1:11. In some embodiments, the proper ratio is about 1:1 (molar). In some embodiments, the period of time for slurrying or stirring the mixtures may be in the range of 0.1-24 hours, 0.2-12 hours, 0.25-6 hours, 0.3-2 hours, 0.4-1 hour, or 0.5-1 hour. In some embodiments, the period of time for slurrying or stirring the mixtures may be about 0.5 hour. In some embodiments, the co-crystal compound may be obtained by drying, filtering, centrifugation, pipetting, or a combination thereof. In some embodiments, the co-crystal compound may be obtained by centrifugation.

The current invention relates to the pharmaceutical use of compounds of the co-crystals of the present invention (e.g. CBP-NMP), and methods of treating or preventing a disease in a subject in need thereof. In some embodiments, the method comprises administering to the subject a pharmaceutical composition comprising a therapeutically effective amount of a compound of one or more of the co-crystals of the present invention (e.g. CBP-NMP).

In some embodiments, the compound of the carboplatin-based co-crystal of the current invention (e.g. CBP-NMP) demonstrates advantageous therapeutic properties. For example, in some embodiments, the compound of the co-crystals of the present invention (e.g. CBP-NMP) may be more effective in killing cancerous or virus-infected cells compared to carboplatin or other known drugs. In other embodiments, the compound of the co-crystals of the present invention (e.g. CBP-NMP) may be less effective in killing cancerous or virus-infected cells compare to carboplatin or other known drugs or have substantially similar effects, but are less toxic to healthy and normal cells, resulting in a net health benefit. For instance, comparing to know platin analogues in the treatment of cancer cells or virus-infected cells, a compound of the CBP-NMP is less toxic and much stable than cisplatin and carboplatin. In some embodiments, the advantageous effects of CBP-NMP may be reduced side effects. In some embodiments, the compound of the CBP-NMP may demonstrate more versatility in pharmaceutical uses, e.g. when compared to carboplatin.

In some embodiments, the compound of the carboplatin-based co-crystal of the current invention (e.g. CBP-NMP) demonstrates advantageous physiochemical properties. For example, in some embodiments, the compound of CBP-NMP may have increased solubility, stability, and bioavailability. For example, in comparison with carboplatin, the compound of CBP-NMP is much more stable and could be stable in solid form of various doses. Meanwhile, water solubility of the compound of CBP-NMP is higher than carboplatin (18 mg/mL), providing significantly more possibility of formulations and administration.

In some embodiments, the $IC_{50}$ of the compound of CBP-NMP to reduce PC-3 cell number is about 19.149 µM; in another embodiment, the $IC_{50}$ of the compound from CBP-NMP to reduce LNCaP cell number is about 42.234 µM; in yet another embodiment, the compound from CBP-NMP shows minimum toxicity to HL-7002 cells, with much higher $IC_{50}$ (e.g. about 10 times) than cisplatin in similar conditions; and in yet another embodiment, the compound from CBP-NMP shows minimum toxicity to HEK293 cells, with much higher $IC_{50}$ (e.g. about 8 times) than cisplatin in similar conditions. In some embodiments, the compound from CBP-NMP demonstrates an $IC_{50}$ of about 19.149 µM to reduce PC-3 cell number, an $IC_{50}$ of about 42.234 µM to reduce LNCaP cell number, $IC_{50}$ of about 20.51 µM to reduce HL-7002 cell number, and $IC_{50}$ of about 55.119 µM to reduce HEK293 cells.

In some embodiments, the $IC_{50}$ of the compound from CBP-NMP to reduce HCT-116 cell number is about 62.026 µM; in another embodiment, the $IC_{50}$ of the compound from CBP-NMP to reduce HT29 cell number is about 32.026 µM; in another embodiment, the compound from CBP-NMP shows minimum toxicity to HL-7002 cells, with much higher $IC_{50}$ (e.g. about 5 times) than 5-FU in similar conditions; and in yet another embodiment, the compound from CBP-NMP shows minimum toxicity to HEK293 cells, with much higher $IC_{50}$ (e.g. about 14 times) than 5-FU in similar conditions. In some embodiments, the compound from CBP-NMP demonstrates an $IC_{50}$ of about 18.357 µM to reduce HCT-116 cell number, an $IC_{50}$ of about 62.026 µM to reduce ACHN cell number, $IC_{50}$ of about 20.51 µM to reduce HL-7002 cell number, and $IC_{50}$ of about 55.119 µM to reduce HEK293 cells.

In some embodiments, the pharmaceutical composition may consist of the compound of the co-crystals of the present invention (e.g. CBP-NMP). In some embodiments, the pharmaceutical composition may comprise the co-crystals of the present invention (e.g. CBP-NMP) and at least one additional therapeutic agent or adjuvant therapy agent. The additional therapeutic agent or adjuvant therapy agent may be selected from but is not limited to: folic acid, coenzyme Q10, curcumin, glutathione (GSH), aloe vera, oryzanol, 5-fluorouracil, bortezomib, or a combination thereof. Depending on the particular disease to be treated, the additional therapeutic agent or adjuvant therapy agent may include drugs already known. In some embodiments, the additional therapeutic agent or adjuvant therapy agent may include drugs that have already been clinically accepted to treat or prevent the disease.

In some embodiments, the pharmaceutical composition may comprise the compound of the co-crystals of the present invention (e.g. CBP-NMP) and a pharmaceutically acceptable carrier or excipient. "Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

In yet another aspect, the amount of the compound of the co-crystals of the present invention (e.g. CBP-NMP) in the pharmaceutical composition administered to a subject may be about 0.005 to 20 mg/kg body weight, about 0.005 to 10 mg/kg body weight, about 0.005 to 5 mg/kg body weight, about 0.005 to 2.5 mg/kg body weight, 0.01 to 20 mg/kg body weight, about 0.01 to 10 mg/kg body weight, about 0.01 to 5 mg/kg body weight, about 0.01 to 2.5 mg/kg body weight, 0.1 to 20 mg/kg body weight, about 0.1 to 10 mg/kg body weight, about 0.1 to 5 mg/kg body weight, or about 0.1 to 2.5 mg/kg body weight. The specific amount of the co-crystal depends on the particular disease to be treated and the subject's specific conditions.

In yet another aspect, the administration of the pharmaceutical composition comprising the compound of the co-crystals of the present invention (e.g. CBP-NMP) may last at least 1, 2, 3, 4, 5, 6, 7, 8, 9, 10, 11, 12, 13, 14, 21, 28, 35, 42, 49, 56, 63, 70, 77, 84, 91 or 98 days. In some embodiments, the administering of the pharmaceutical composition may last at least one week. In some embodiments, the administering of the pharmaceutical composition may last at least two weeks. The specific period of administration depends on the particular disease to be treated and the subject's specific conditions.

The present invention in various aspects and embodiments involves uses of the co-crystals of the present invention (e.g. CBP-NMP) for the prevention or treatment of various diseases and methods of treating or preventing the diseases by administering a pharmaceutical composition comprising the compound of the co-crystals of the present invention (e.g. CBP-NMP). The diseases to be treated or prevented include but are not limited to cancers and viral infections.

In some embodiments, the disease is a cancer. In some embodiments, the cancer is selected from: bladder cancer, non-small cell lung cancer, cervical cancer, anal cancer, pancreatic cancer, squamous cell carcinoma including head and neck cancer, renal cell carcinoma, basal-cell skin cancer (BCC), squamous-cell skin cancer (SCC), melanoma, ovarian cancer, small cell lung cancer, endometrial cancer, glioblastoma, astroycytoma, oligodendroglioma, ependymoma, neurofibrosarcoma, meningioma, gastrointestinal stromal tumor, breast cancer, lung cancer, colorectal cancer, thyroid cancer, bone sarcoma, stomach cancer, oral cavity cancer, oropharyngeal cancer, gastric cancer, renal adenocarcinoma, liver cancer, prostate cancer, esophageal cancer, testicular cancer, gynecological cancer, colorectal cancer, brain cancer, leukemia, leucocythemia, chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, and myelofibrosis.

In some embodiments, the pharmaceutical composition comprising the compound of the co-crystals of the present invention (e.g. CBP-NMP) may be used to prevent or treat prostate cancer, colorectal cancer, renal adenocarcinoma or leucocythemia. In some embodiments, the therapeutically effective amount of the co-crystals of the present invention to prevent or treat cancer may about 0.01 to about 10 mg/kg body weight. In another embodiment, the therapeutically effective amount of the compound of the co-crystals of the present invention to prevent or treat cancer is about 0.01 to about 5 mg/kg body weight.

In some embodiments, the disease is a viral infection. In some embodiments, the virus is a DNA virus or an RNA virus. For example, in some embodiments the virus may be a DNA virus such as but not limited to adenovirus, herpes simplex virus, human pepillomavrus, VITAMIN K virus, smallpox virus, hepatitis B virus (HBV), and parvovirus B19. In other embodiments, the virus may be an RNA virus such as but not limited to human astrovirus, norwalk virus, hepatitis A virus (HAV), severe acute respiratory syndrome virus, hepatitis C virus (HCV), yellow fever virus, dengue virus, West Nile virus, TBE virus, rubella virus, hepatitis E virus (HEV), human immunodeficiency virus (HIV), influenza virus, Lassa virus (LASV), Crimean-Congo hemorrhagic fever virus, Hantaan virus, Ebola virus, Marburg virus, Measles virus, mumps virus, parainfluenza virus, respiratory syncytial virus, rabies virus, and hepatitis D virus (HDV), rotavirus, orbivirus, coltivirus, Banna virus.

In some embodiments, the pharmaceutical composition may be used to prevent or treat viral infections caused by HBV, HCV, HIV or Hantaan virus. In some embodiments, the therapeutically effective amount of the compound of the co-crystals of the present invention (e.g. CBP-NMP) to prevent or treat viral infection is about 0.01 to about 10 mg/kg body weight. In another embodiment, the therapeutically effective amount of the compound of the co-crystals of the present invention (e.g. CBP-NMP) to prevent or treat cancer is about 0.01 to about 5 mg/kg body weight.

In some embodiments, the present invention provides a method of treating, preventing, reducing or alleviating the symptoms of, and/or slowing or halting the progress of prostate cancer, colorectal cancer, renal adenocarcinoma or leucocythemia in a subject in need thereof, the method comprising administrating to the subject an effective amount of a pharmaceutical composition comprising the compound of the co-crystals of the present invention (e.g. CBP-NMP). In some embodiments, the pharmaceutical composition consists of the compound of the co-crystals of the present invention (e.g. CBP-NMP). In some embodiments, the pharmaceutical composition further comprises at least one additional therapeutic agent or adjuvant therapy agent. In a specific embodiment, the additional therapeutic agent or adjuvant therapy agent may be selected from: folic acid, coenzyme Q10, curcumin, glutathione (GSH), aloe vera, oryzanol, 5-fluorouracil, and bortezomib. In some embodiments, the pharmaceutical composition comprises the compound of the co-crystals of the present invention (e.g. CBP-NMP) and a pharmaceutically acceptable carrier or excipient.

In some embodiments, the present invention provides a method of treating, preventing, reducing or alleviating the symptoms of, and/or slowing or halting the progress of viral infections caused by HBV, HCV, HIV or Hantaan virus in a subject in need thereof, the method comprising administrating to the subject an effective amount of a pharmaceutical composition comprising the compound of the co-crystals of the present invention (e.g. CBP-NMP). In some embodiments, the pharmaceutical composition consists of the compound of the co-crystals of the present invention (e.g. CBP-NMP). In some embodiments, the pharmaceutical composition further comprises at least one additional therapeutic agent or adjuvant therapy agent. In a specific embodiment, the additional therapeutic agent or adjuvant therapy agent may be selected from: folic acid, coenzyme Q10, curcumin, glutathione (GSH), aloe vera, oryzanol, 5-fluorouracil, and bortezomib. In some embodiments, the pharmaceutical composition comprises the compound of the co-crystals of the present invention (e.g. CBP-NMP) and a pharmaceutically acceptable carrier or excipient.

In some embodiments, for prevention or treatment of prostate cancer, colorectal cancer, renal adenocarcinoma or leucocythemia, the pharmaceutical composition comprising the compound of the CBP-NMP is administered with infusion, injections or via the oral route. In some embodiments, for prevention or treatment of prostate cancer, colorectal cancer, renal adenocarcinoma or leucocythemia, the pharmaceutical composition comprising the compound of the CBP-NMP is administered for at least one, two or three weeks.

In some embodiments, for prevention or treatment of viral infections caused by HBV, HCV, HIV or Hantaan virus, the pharmaceutical composition comprising the CBP-NMP is administered with infusion, injections or via the oral route. In some embodiments, for prevention or treatment of viral infections caused by HBV, HCV, HIV or Hantaan virus, the pharmaceutical composition comprising the compound of the CBP-NMP is administered for at least one, two or three weeks.

EXAMPLES

The effects of the co-crystal of the present invention on certain diseases are shown in the following example. In addition, the process of making CBP-NMP and the physiochemical properties of CBP-NMP are also described. These examples do not in any way limit the scope of the invention.

Through the screening of the co-crystal formers that can be combined with carboplatin, cyclic amides were found to be strong candidates. The resulting co-crystal meet partly or completely the targeted objects, such as increased solubility, stability and bioavailability and more versatile in pharmaceutical use compared to carboplatin or other platin compounds.

In comparison with carboplatin, the co-crystal of the current inventions is more stable and can be stable in solid forms. The co-crystal prepared from co-crystal former carboplatin with N-methyl-2-pyrrolidone (NMP), termed as CBP-NMP, is presented as an example.

In comparison to the reported platin analogues for the treatment of cancer cells, some of the co-crystals of the current inventions are less toxic and much stable than cisplatin and carboplatin.

The inventors have determined that the formation of crystalline polymorphic forms and form I was confirmed for the co-crystal of carboplatin with NMP. Amorphous forms of the co-crystal and other forms may be existent using different crystallization process. Form I of the co-crystal of carboplatin with NMP in the invention was confirmed by XRPD, DSC, SEM and other characterization methods.

The Effects of CBP-NMP on Prostate Cancer Cells

The co-crystal CBP-NMP was tested in the treatment of prostate cancers docetaxel and cisplatin, widely accepted drugs for prostate cancer patients.

PC-3 cells are a cell line derived from advanced prostate cancer patient with bone metastasis and are characteristic of prostate cancer such as prostate small cell carcinoma. PC-3 cells were treated with drugs (CBP-NMP, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 1.

CBP-NMP showed superior effect to reduce PC-3 cell number compared to docetaxel. In particular, the $IC_{50}$ of CBP-NMP was 19.149 μM, while $IC_{50}$ of docetaxel and cisplatin were 49.924 μM and 2.489 μM respectively (FIG. 1).

LNCaP cells are a cell line derived from advanced prostate cancer patient with lymph node metastasis. LNCaP cells were treated with drugs (CBP-NMP, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 2.

Figure 2:
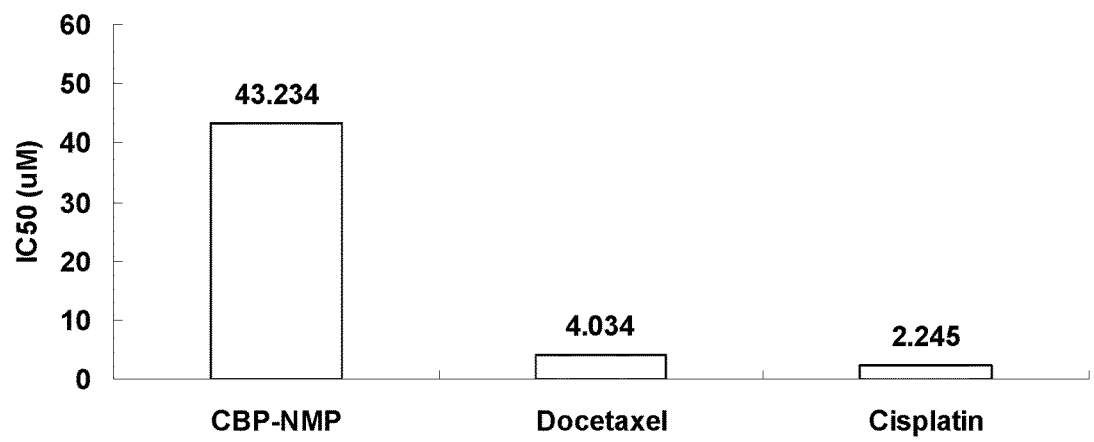
FIG. 2 shows the $IC_{50}$ of CBP-NMP and the control chemicals docetaxel and cisplatin in LNCaP prostate cancer cell line.

For LNCaP cells, the $IC_{50}$ of CBP-NMP was 43.234 μM; the $IC_{50}$ of docetaxel and cisplatin were 4.034 μM and 2.245 μM respectively (FIG. 2).

Figure 3:
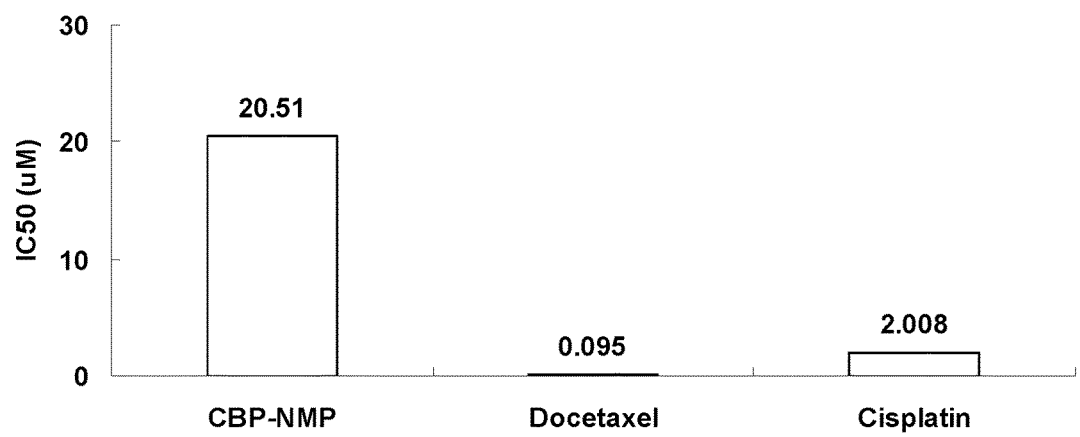
FIG. 3 shows the $IC_{50}$ of CBP-NMP and the control chemicals docetaxel and cisplatin in fetal hepatocytes HL-7002.

HL-7002 cells are an immortalized human fetal hepatic cell line. HL-7002 cells were treated with drugs (CBP-NMP, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 3.

For HL-7002 cells, CBP-NMP was detected to have minimum toxicity—about 1/216 of docetaxel and about 1/10 of cisplatin in similar conditions. The $IC_{50}$ of CBP-NMP was 20.51 μM; the $IC_{50}$ of docetaxel and cisplatin were 0.095 μM and 2.008 μM respectively (FIG. 3).

Figure 4:
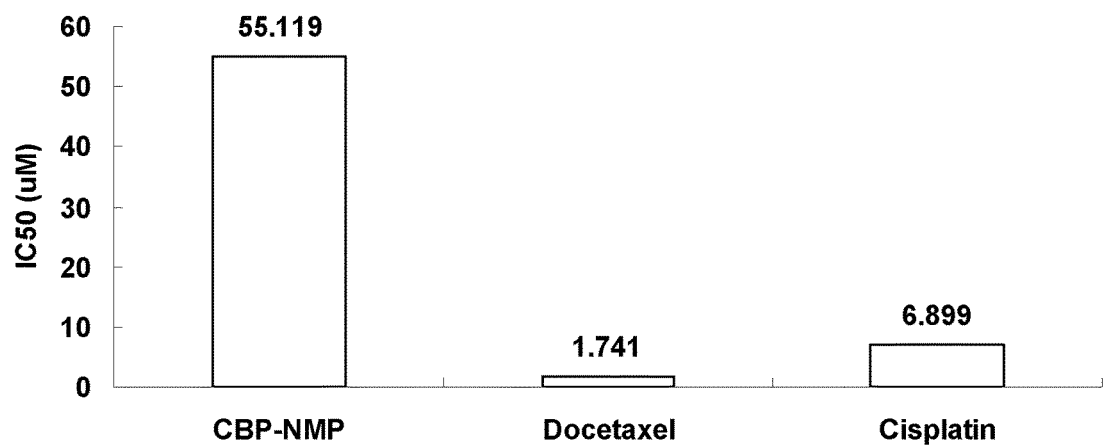
FIG. 4 shows the $IC_{50}$ of CBP-NMP and the control chemicals docetaxel and cisplatin in human embryonic kidney cell line HEK293.

HEK293 cells are an immortalized human fetal kidney cell line. HEK293 cells were treated with drugs (CBP-NMP, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 4.

For HEK293 cells, CBP-NMP showed a low level of toxicity—about 1/32 of docetaxel and about 1/8 of cisplatin in similar conditions. The value of $IC_{50}$ of CBP-NMP was 55.119 μM, while $IC_{50}$ of Docetaxel and Cisplatin is 1.741 μM and 6.899 μM, respectively (FIG. 4.).

Methods and Strategies:

Cell culture: Prostate cancer cell lines LNCaP and PC-3 were purchased from ATCC (Manassas, Va.). The fetal hepatocytes HL-7002 and human embryonic kidney cells HEK393 were purchased from ATCC. The cells were cultured in RPMI+5% Fetal Bovine Serum (FBS).

Drug treatment and cell viability (MTS) assay: The cells (105/100 mL/well) were cultured in a 96 well plate, and treated with drugs (e.g. CBP-NMP) at step-wise concentrations from 0.01 to 300 μM. The cells treated with the solvents were used as the negative control, and cisplatin and docetaxel were used as the positive controls. The cells were monitored daily, and the cell viability was evaluated with the Promega CellTiter 96 AQueous One Solution Cell Proliferation Assay (Promega, Madison, Wis., USA) according to the manufacture manuals. The cell viability was monitored at OD490 reading in a bio-spectrometer (Perkin Elmer, Waltham, Mass., USA).

Data analysis: The OD490 reading data were collected hourly from 1 h to 4 h after the addition of lysis buffer. The index of cell growth repression ratio was obtained by comparing the OD490 data of treatment to the negative control. The drug response rate $IC_{50}$ was calculated with the SPSS 16.0.

Summary of Effects:

For PC-3, a cell line derived from advanced prostate cancer patient with bone metastasis, CBP-NMP showed a superior cellular toxicity with Docetaxel, but weaker than for Cisplatin. For LNCaP, a cell line derived from advanced prostate cancer patient with lymph node metastasis, the cellular toxicity of CBP-NMP is weaker than Docetaxel and Cisplatin. For HL-7002, an immortalized human fetal hepatic cell line, CBP-NMP was detected to have a low level of cellular toxicity, but much weaker than Docetaxel and Cisplatin. For HEK293, an immortalized human fetal kidney cell line, CBP-NMP was detected to have a low level of toxicity, but much weaker than for Docetaxel and Cisplatin.

The Effects of CBP-NMP on Colorectal Cancer Cells

The co-crystal CBP-NMP was tested in the treatment of colorectal cancers in comparison to oxaliplatin and fluorouracil (5-FU), widely used drugs in treating colorectal cancer patients.

Figure 5:
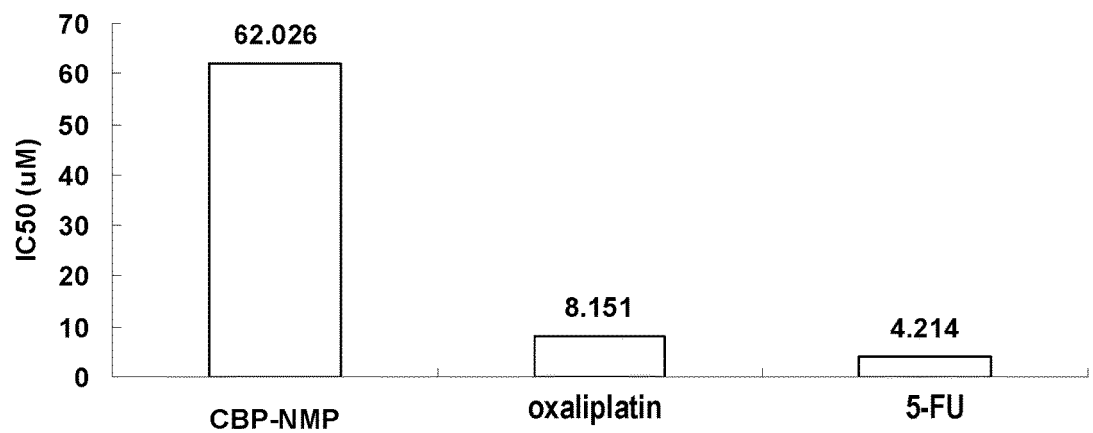
FIG. 5 shows the $IC_{50}$ of CBP-NMP and the control chemicals oxaliplatin and 5-FU in colorectal cancer cell line HCT-116.

HCT-116 cells are a colorectal cancer cell line. HCT-116 cells were treated with drugs (CBP-NMP, 5-FU, or oxaliplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 5.

For HCT-116 cells, the effect to reduce cell number by CBP-NMP is than 5-FU and oxaliplatin. $IC_{50}$ of CBP-NMP was 62.026 μM; $IC_{50}$s of oxaliplatin and 5-FU were determined to be 8.151 μM and 4.214 μM respectively (FIG. 5).

Figure 6:
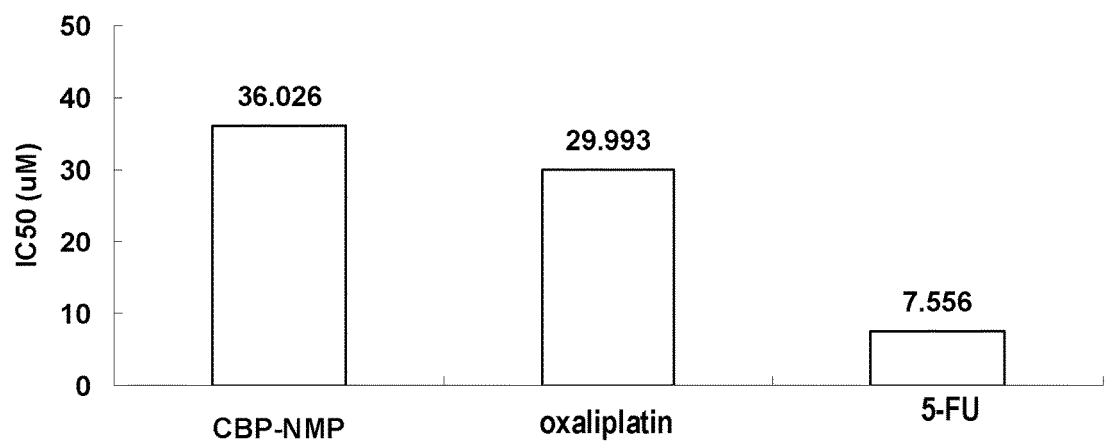
FIG. 6 shows the $IC_{50}$ of CBP-NMP and the control chemicals oxaliplatin and 5-FU in colorectal cancer cell line HT-29.

HT29 cells are a colorectal cancer cell line. HT29 cells were treated with drugs (CBP-NMP, 5-FU, or oxaliplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 6.

For HT29 cells, $IC_{50}$ of CBP-NMP was 36.026 μM; $IC_{50}$s of oxaliplatin and 5-FU were determined to be 29.993 μM and 7.556 μM respectively (FIG. 6).

Figure 7:
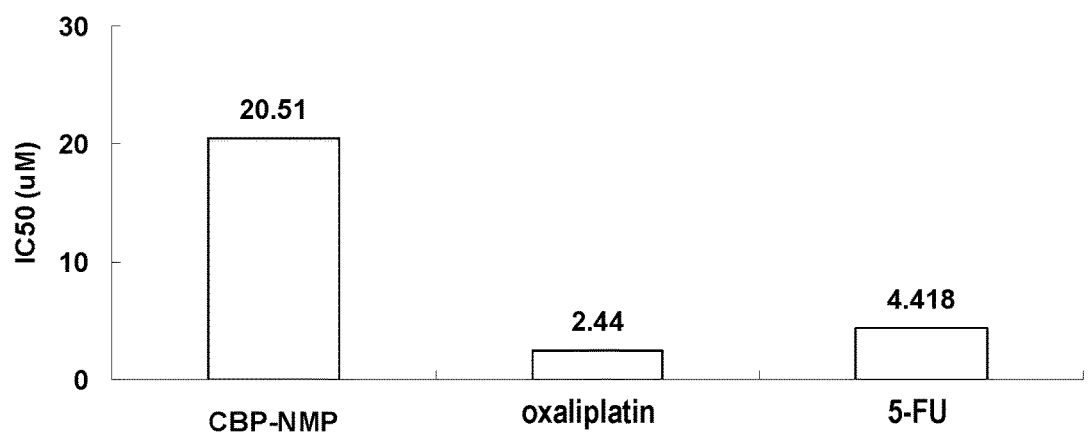
FIG. 7 shows the $IC_{50}$ of CBP-NMP and the control chemicals oxaliplatin and 5-FU in fetal hepatocytes HL-7002.

HL-7002 hepatocyte cell line cells were treated with drugs (CBP-NMP, 5-FU, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 7.

For HL-7002 cells, only a low level of toxicity of CBP-NMP was detected. In similar conditions, the toxicity of CBP-NMP was about ⅕ of that of oxaliplatin and about ⅛ of that of 5-FU. $IC_{50}$ of CBP-NMP was 20.51 μM; $IC_{50}$s of oxaliplatin and 5-FU were 2.44 μM and 4.418 μM, respectively (FIG. 7).

HEK293 kidney cell line cells were treated with drugs (CBP-NMP, 5-FU, or oxaliplatin) at step-wise concentrations, and the cell viability was evaluated with the CellTiter 96 AQueous One Solution Cell Proliferation Assay from Promega Corp. (Madison, Wis., USA).

Figure 8:
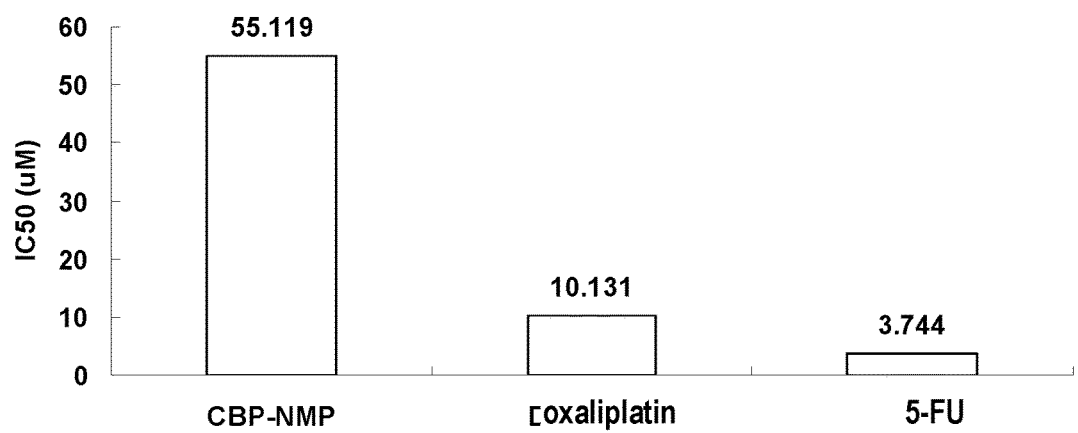
FIG. 8 shows the $IC_{50}$ of CBP-NMP and the control chemicals oxaliplatin and 5-FU in human embryonic kidney cell line HEK293.

The index of cell growth repression ratio was obtained by comparing the OD490 data of treatment group to the negative control. The drug response rate $IC_{50}$ was calculated with the SPSS 16.0 system. The results are shown in FIG. 8.

For HEK293, only minimum toxicity of CBP-NMP was detected. In similar conditions, the toxicity of CBP-NMP was about ⅕ of that of oxaliplatin and about ⅕ of that of 5-FU. $IC_{50}$ of CBP-NMP was 55.119 μM; $IC_{50}$s of $IC_{50}$ of oxaliplatin and 5-FU were 10.131 μM and 3.744 μM respectively (FIG. 8).

Methods and Strategies:

Cell culture: Colorectal cancer cell lines HCT-116 and HT29 were purchased from ATCC (Manassas, Va.). The fetal hepatocytes HL-7002 and human embryonic kidney cells HEK393 were purchased from ATCC. The cells were cultured in RPMI+5% Fetal Bovine Serum (FBS).

Drug treatment and cell viability (MTS) assay: The cells (105/100 mL/well) were cultured in a 96 well plate, and treated with drugs (e.g. CBP-NMP) at step-wise concentrations from 0.01 to 300 μM. The cells treated with the solvents were used as the negative control, and cisplatin and docetaxel were used as the positive controls. The cells were monitored daily, and the cell viability was evaluated with the Promega CellTiter 96 AQueous One Solution Cell Proliferation Assay (Promega, Madison, Wis., USA) according to the manufacture manuals. The cell viability was monitored at OD490 reading in a bio-spectrometer (Perkin Elmer, Walthan, Mass., USA).

Data analysis: The OD490 reading data were collected hourly from 1 h to 4 h after the addition of lysis buffer. The index of cell growth repression ratio was obtained by comparing the OD490 data of treatment to the negative control. The drug response rate $IC_{50}$ was calculated with the SPSS 16.0.

Summary of Effects:

For colorectal cancer cell line HCT-116, CBP-NMP showed weaker toxicity than for Oxaliplatin and 5-FU. For colorectal cancer cell line HT29, CBP-NMP showed a little weaker toxicity than for Oxaliplatin, and weaker than for 5-FU. For HL-7002, an immortalized human fetal hepatic cell line, CBP-NMP was detected to have a low level of toxicity. For HEK293, an immortalized human fetal kidney cell line, CBP-NMP was detected to have a low level of toxicity.

Process to Produce the Co-Crystals

The co-crystals of the current invention were formed from carboplatin and cyclic amides as co-crystal formers. A comprehensive co-crystal screening was performed via slurry/stirring, heating and cooling, rotary evaporation, lyophilization, cooling, and evaporation.

One co-crystal of the current invention, CBP-NMP, was first found from the mixture of dicycloplatin (DCP), a super molecule composed of carboplatin (CBP) and 1,1-cyclobutane dicarboxylate (CBDCA)) and N-methyl-2-pyrrolidone (NMP). By X-Ray powder diffraction (XRPD), thermal gravimetric analysis (TGA) and differential scanning calorimetry (DSC), it was determined that the co-crystal (804609-38-A9) formed from DCP in NMP solution was a new crystal and it was confirmed that the newly formed co-crystal was a co-crystal of carboplatin (CBP) and NMP on a 1:1 mol ratio.

Figure 9:
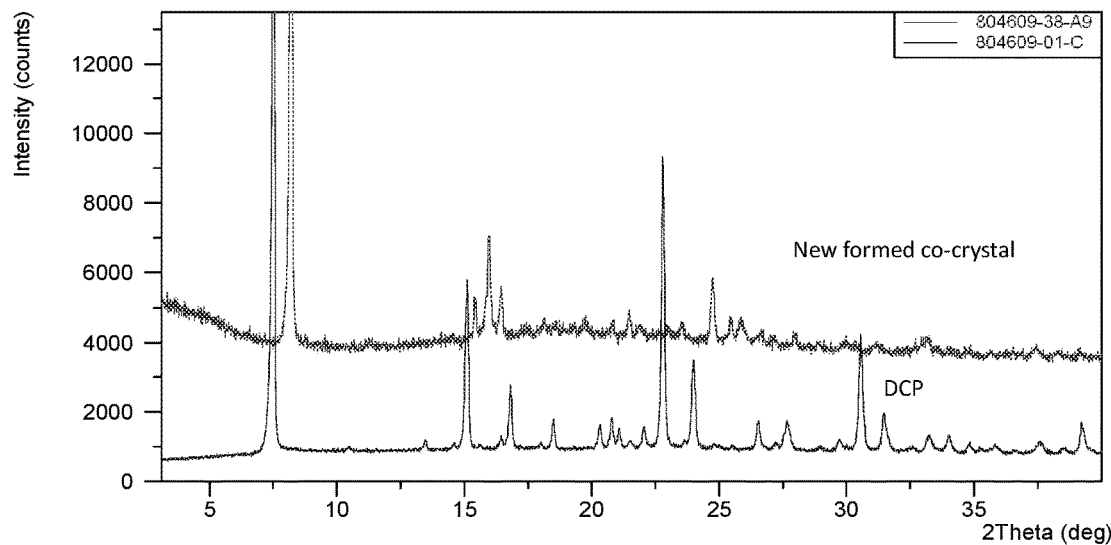
FIG. 9 shows the X-ray powder diffraction (XRPD) pattern of DCP and a new-crystal from a mixture of DCP in NMP (804609-38-A9).

It was later confirmed that the new crystal (804609-38-A9) prepared from DCP in NMP solution was the same co-crystal prepared from carboplatin in NMP (804609-44-B) (FIG. 9). In particular, a mixture of 515 mg of carboplatin and 4 mL of N-methyl-2-pyrrolidone (NMP) were stirred around 20° C. for 5 hours. Then the reaction was cooled to 0-5° C. and stirred over 5 hours. The resulting crude crystal was obtained by filtering and was washed by pre-cooled ethanol and heptane. After being dried in vacuum, 507 mg of pure crystal (CBP-NMP) was obtained. It was analyzed by high performance liquid chromatography (HPLC), MS, $^1$H-NMR, XRPD, DSC and single x-ray characterization. The characterization indicated 1:1 ratio of carboplatin to N-methyl-2-pyrrolidone in this co-crystal structure.

Figure 11:
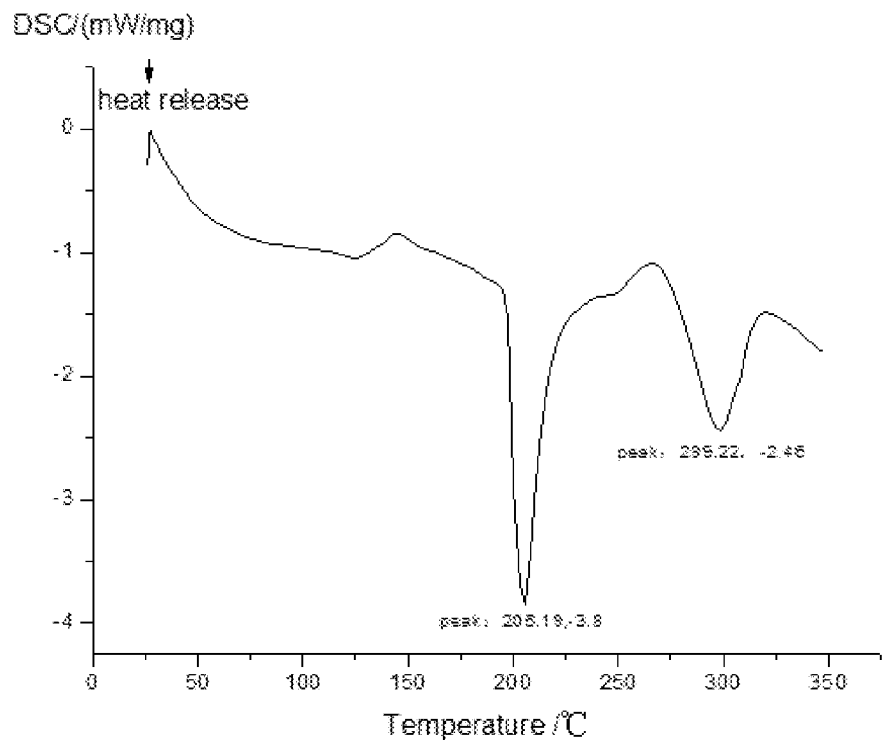
FIG. 11 shows the differential scanning calorimetry (DSC) of a CBP-NMP sample (804609-44-B).
Figure 12:
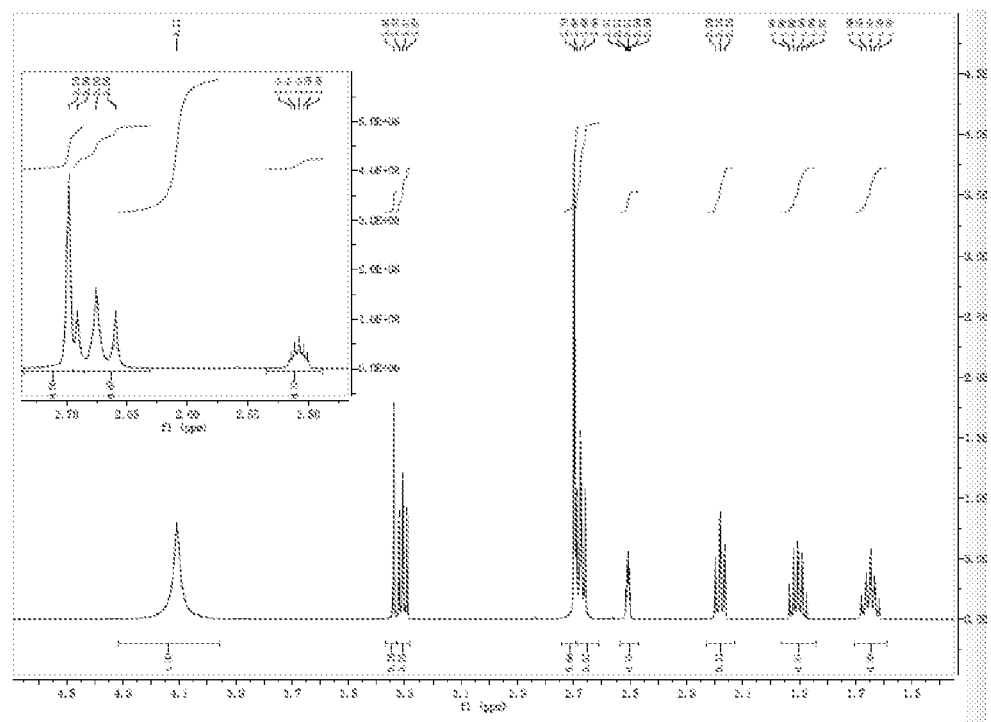
FIG. 12 shows proton nuclear magnetic resonance ($^1$H-NMR) spectra of a CBP-NMP sample (804609-44-B).
Figure 15:
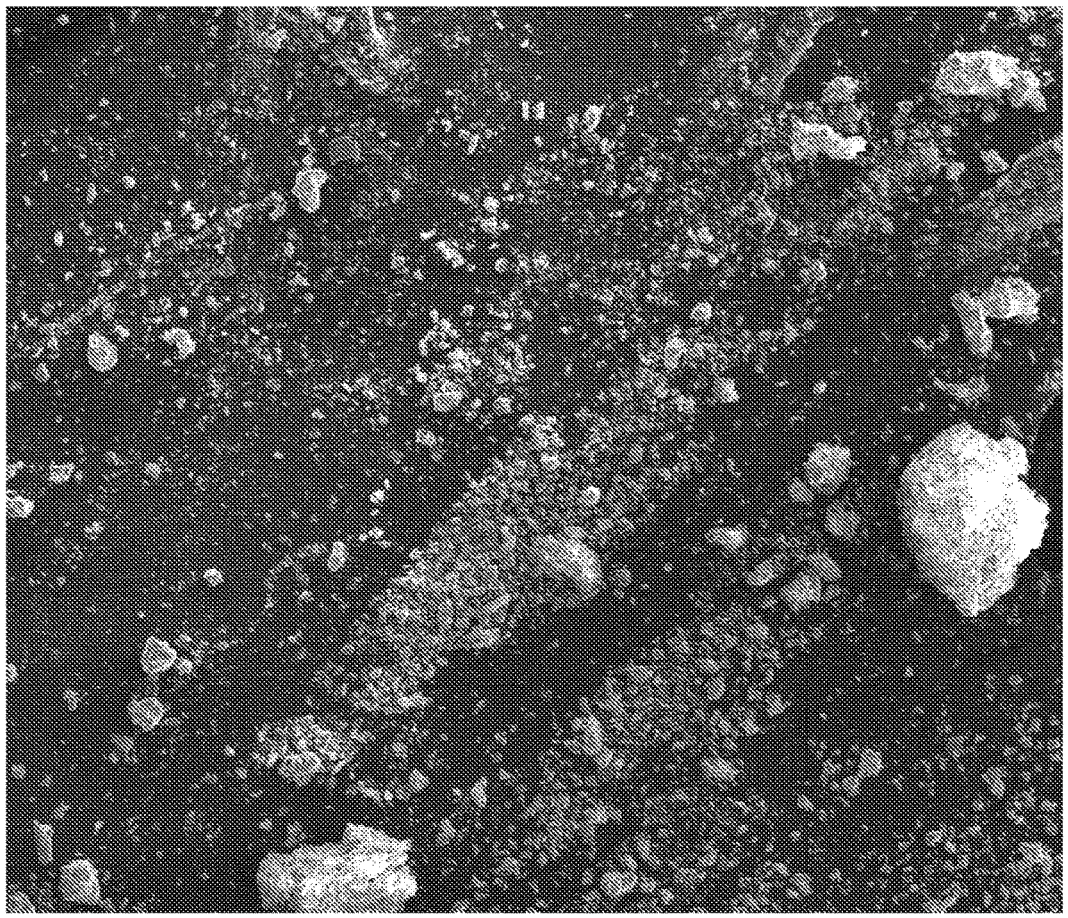
FIG. 15 shows scanning electron microscope (SEM) results of a CBP-NMP sample.
Figure 16:
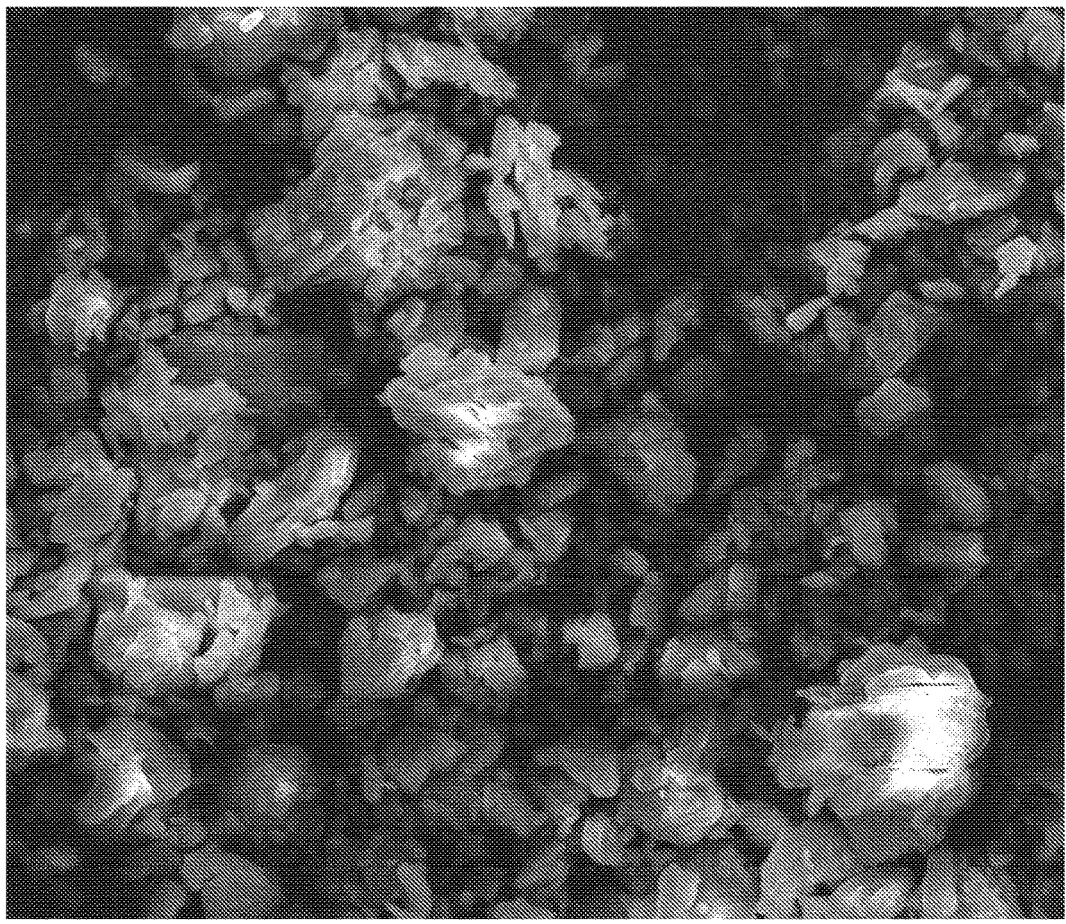
FIG. 16 shows SEM results of a CBP-NMP sample.
Figure 17:
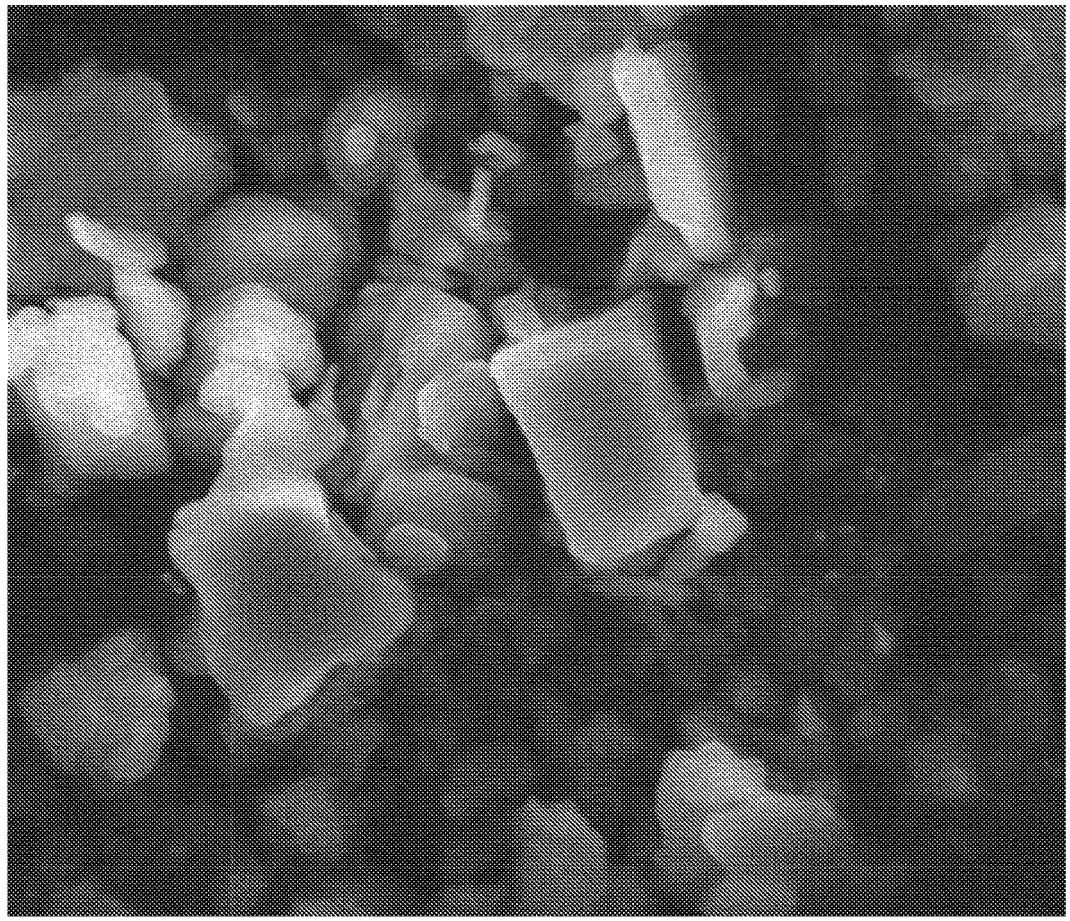
FIG. 17 shows SEM results of a CBP-NMP sample.

The CBP-NMP structure was characterized by XRPD (FIG. 10), differential scanning calorimetry (DSC) (FIG. 11), proton nuclear magnetic resonance ($^1$H-NMR) (FIG. 12) and scanning electron microscopy (SEM) (FIG. 15-17). One form of the CBP-NMP co-crystal, as indicated in the XRPD pattern of 804609-44-B in FIG. 10, may be referred to as Form A.

Figure 13:
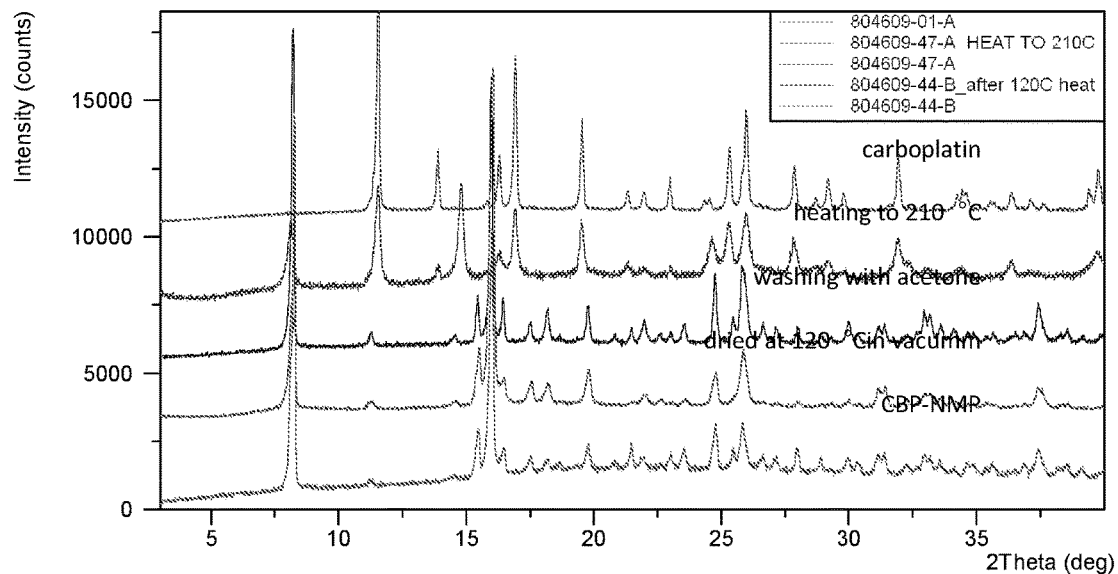
FIG. 13 shows a XRPD of a CBP-NMP sample (804609-44-B) after treatment.
Figure 14:
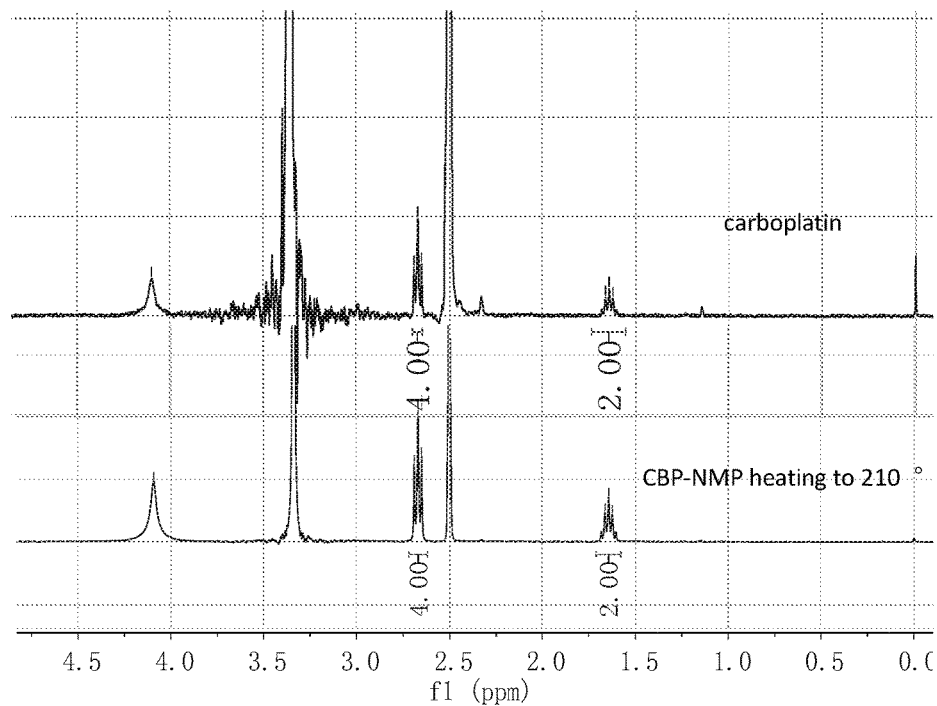
FIG. 14 shows a $^1$H NMR of a CBP-NMP sample (804609-44-B) after heating to 210° C.

When CBP-NMP was gradually heated at different temperatures, it was discovered that CBP-NMP was converted to carboplatin (CBP) on 210° C. (FIG. 13). NMP was removed from the co-crystal CBP-NMP at this point. Further $^1$H NMR characterization of the formed sample from heating CBP-NMP to 210° C. confirmed the change (FIG. 14).

A number of other co-crystal are also obtained.

Mixtures of 515 mg of carboplatin, 4.2 mL of 1-butylpyrrolidine-2-one and 3.0 mL of $CH_2Cl_2$ are stirred around 20° C. for 5 hours. Then the reaction is cooled to 0-5° C. and stirred over 5 hours. The resulting crude crystal is obtained by filtering and is washed by pre-cooled $CH_2Cl_2$ and heptane. After being dried in vacuum, 443 mg of pure crystal is obtained. It is analyzed by HPLC, MS and $^1$H-NMR. The characterization indicated 1:1 ratio of carboplatin to 1-butylpyrrolidine-2-one in this co-crystal structure.

Mixtures of 550 mg of carboplatin, 3.5 g of 1,5-dimethyl-2-pyrrolidine and 6.0 mL of distilled water are stirred around 20° C. for 5 hours. Then 15 mL of distilled water is added to dissolve the mixtures. The obtained solution is filtered through 0.45 um filter and the solution is dried by stepwise cooling. After cooling dry, the resulting crude crystal is treated with ethanol and heptane and 415 mg of pure crystal is obtained. It is analyzed by HPLC, MS and $^1$H-NMR. The characterization indicated 1:1 ratio of carboplatin to 1,5-dimethyl-2-pyrrolidine in this co-crystal structure.

Mixtures of 515 mg of carboplatin, 3.1 g of 1-benzylpiperidine-2,4-dione and 3.0 mL of toluene are stirred around 20° C. for 5 hours. Then the reaction is cooled to 0-5° C. and stirred over 5 hours. The resulting crude crystal is obtained by filtering and is washed by pre-cooled toluene and heptane. After dried in vacuum, and 478 mg of pure crystal is obtained. It is analyzed by HPLC, MS and $^1$H-NMR. The characterization indicated 1:1 ratio of carboplatin to 1-benzylpiperidine-2,4-dione in this co-crystal structure.

Mixtures of 515 mg of carboplatin and 4 mL of 1-vinyl-2-pyrrolidone are stirred around 20° C. for 5 hours. Then the reaction is cooled to 0-5° C. and stirred over 5 hours. The resulting crude crystal is obtained by filtering and is washed by pre-cooled ethanol and heptane. After being dried in vacuum, 507 mg of pure crystal is obtained. It is analyzed by HPLC, MS, $^1$H-NMR. The characterization indicated 1:1 ratio of carboplatin to 1-vinyl-2-pyrrolidone in this co-crystal structure.

Mixtures of 515 mg of carboplatin, 810 mg of N-vinyl-ε-caprolactam and 3.0 mL of $CH_2Cl_2$ are stirred around 20° C. for 5 hours. Then the reaction is cooled to 0-5° C. and stirred over 5 hours. The resulting crude crystal is obtained by filtering and is washed by pre-cooled $CH_2Cl_2$ and heptane. After being dried in vacuum, 522 mg of pure crystal is obtained. It is analyzed by HPLC, MS and $^1$H-NMR. The characterization indicated 1:1 ratio of carboplatin to N-vinyl-ε-caprolactam in this co-crystal structure.

Mixtures of 515 mg of carboplatin, 1.2 g of N-methyl-ε-caprolactam and 3.0 mL of $CH_2Cl_2$ are stirred around 20° C. for 5 hours. Then the reaction is cooled to 0-5° C. and stirred over 5 hours. The resulting crude crystal is obtained by filtering and is washed by pre-cooled $CH_2Cl_2$ and heptane. After being dried in vacuum, 488 mg of pure crystal is obtained. It is analyzed by HPLC, MS and $^1$H-NMR. The characterization indicated 1:1 ratio of carboplatin to N-methyl-ε-caprolactam in this co-crystal structure.

Mixtures of 515 mg of carboplatin, 2.5 g of laurocapram and 5.0 mL of $CH_2Cl_2$ are stirred around 20° C. for 5 hours. Then the reaction mixtured is concentrated and cooled to 0-5° C. and 10 mL of heptane is added and stirred over 5 hours. The resulting crude crystal is obtained by filtering and is washed by pre-cooled $CH_2Cl_2$ and heptane. After being dried in vacuum, 553 mg of pure crystal is obtained. It is analyzed by HPLC, MS and $^1$H-NMR. The characterization indicated 1:1 ratio of carboplatin to laurocapram in this co-crystal structure.

Analytical Methods

X-Ray Powder Diffraction (XRPD):

Polarized light microscopic picture was captured at room temperature (RT). X-ray intensity data were collected at 296(2) K using a Bruker APEX II CCD diffractometer (Mo Kα radiation, λ=0.71073 Å). XRPD pattern was collected by Panalytical Empyrean system at RT. Direct methods structure solution, difference Fourier calculations and full-matrix least-squares refinement against F2 were performed with SHELXTL and OLEX2, See Sheldrick G M. *Acta Crystallogr A*, 64: 112-122, 2008; and O. V. Dolomanov, et al. *J. Appl. Cryst.* 42, 339-341, 2009; and Brandenburg, K. DIAMOND, 1999, Crystal Impact GbR, Bonn, Germany. Molecular graphics were created according to Brandenburg, K. *DIAMOND*, 1999, Crystal Impact GbR, Bonn, Germany.

Analytical Instrument: Panalytical Empyrean. The X-ray powder diffraction was conducted by mounting a sample of the crystalline material on a Si single crystal low-background holder and spreading out the sample into a thin layer with the aid of a microscope slide. The 2θ position was calibrated against Panalytical 640 Si powder standard. The sample was irradiated with X-rays generated by a copper long-fine focus tube operated at 45 kV and 40 mA with a wavelength of Kα1=1.540589 angstroms and Kα2=1.544426 angstroms (Kα2/Kα1 intensity ratio is 0.50). The collimated X-ray source was passed through a programmed divergence slit set at 10 mm and the reflected radiation directed through a 5.5 mm anti-scatter slit. The sample was exposed for 16.3 seconds per 0.013° 2-theta increment (continuous scan mode) over the range 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software.

Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a limited effect. Hence the diffraction pattern data presented are not intended to be limited to the absolute values.

Differential Scanning Calorimetry (DSC)

DSC was used as a thermoanalytical method to measure the difference in the amount of heat required to increase the temperature of a sample and reference was measured as a function of temperature. The general process of DSC is known and the specific instruments and conditions in the following Examples were as follows:

Analytical Instrument: TA Instruments Q2000 DSC;

Heating rate: 10° C. per minute; and Purge gas: nitrogen.

Thermal Gravimetric Analysis (TGA)

TGA was used to measure changes in physical and chemical properties of samples as a function of increasing temperature (with constant heating rate), or as a function of time (with constant temperature and/or constant mass loss). The general process of TGA is known and the specific instruments and conditions in the following Examples were as follows:

Analytical Instrument: TA Instruments Q5000 TGA;

Heating rate: 10° C. per minute; and

Purge gas: nitrogen.

Sample Pharmaceutical Composition Comprising the Co-Crystal and its Administration Aqueous or solid pharmaceutical composition of the present invention comprises an effective amount of the co-crystal of the current invention, e.g. CBP-NMP, with or without an appropriate amount of at least one additional therapeutic agent or adjuvant therapy agent. The co-crystal, as well as the therapeutic agent or adjuvant therapy agent, may be dissolved or dispersed in a pharmaceutical acceptable carrier or aqueous media.

Depending on the particular cancer to be treated, administration of pharmaceutical composition according to the present invention can via any common route as long as the target issue is available via the route. For example, the pharmaceutical composition may be administered by infusion, injection, or via the oral route.

A number of pharmaceutical compositions were produced:

Pharmaceutical composition sample A: 70 g of CBP-NMP was dissolved in pre-treated normal saline or 5% of aqueous glucose (in water) and the final volume of the solution was adjusted to 5.0 L. Then the solution was filtered through 0.22 um filter and dispersed into ample bottles with 50.0 mL in each.

Pharmaceutical composition sample B: 70 g of CBP-NMP and 20 g of glutathione (GSH) were dissolved in pre-treated normal saline or 5% aqueous glucose (in water) and final volume of the solution was adjusted to 5.0 L. Then the solution was filtered through 0.22 um filter and dispersed into ample bottle with 50.0 mL solution each.

What is claimed is:

1. A co-crystal comprising carboplatin (CBP) and a cyclic amide, wherein the cyclic amide is N-methyl-2-pyrrolidone (NMP), and the carboplatin and the cyclic amide are bonded at a 1:1 ratio.

2. The co-crystal of claim 1, wherein the co-crystal has an x-ray diffraction pattern comprising peaks at diffraction angles 2-Theta of 16.0° and 24.5°±0.2.

3. The co-crystal of claim 1, wherein the co-crystal comprises one or more crystalline polymorphic forms.

4. A pharmaceutical composition comprising the co-crystal of claim 1.

5. The pharmaceutical composition of claim 4, wherein the co-crystal comprises one or more polymorphic forms.

6. The pharmaceutical composition of claim 4, further comprising at least one therapeutic agent or adjuvant therapy agent.

7. The pharmaceutical composition of claim 6, wherein the therapeutic agent or adjuvant therapy agent is selected from the group consisting of folic acid, coenzyme Q10, curcumin, glutathione (GSH), aloe vera, oryzanol, 5-fluorouracil, and bortezomib.

8. A method of treating cancer in a subject in need thereof, comprising administering to the subject an aqueous composition comprising an effective amount of the co-crystal of claim 2 and pharmaceutically acceptable amount of at least one therapeutic agent or adjuvant therapy agent dissolved or dispersed in a pharmaceutically acceptable carrier or aqueous media.

9. A method of treating cancer in a subject in need thereof, comprising administering to the subject the pharmaceutical composition of claim 4, wherein the co-crystal is administered in a therapeutically effective amount.

10. The method of claim 9, wherein the cancer is selected from the group consisting of prostate cancer, colorectal cancer, renal adenocarcinoma and leucocythemia.

11. The method of claim 10, wherein the cancer is prostate cancer.

12. The method of claim 10, wherein the cancer is colorectal cancer.

13. The method of claim 10, wherein the cancer is renal adenocarcinoma.

14. The method of claim 10, wherein the cancer is leucocythemia.

15. A method of treating a virus infection in a subject in need thereof, comprising administering to the subject the pharmaceutical composition of claim 7, wherein the co-crystal is administered in a therapeutically effective amount.

16. The method of claim 15, wherein the virus infection is caused by hepatitis B virus (HBV), hepatitis C virus (HCV), human immunodeficiency virus (HIV), or Hantaan virus.

17. The method of claim 9, wherein the therapeutically effective amount of the co-crystal is about 0.01 to about 10 mg/kg body weight.

18. The method of claim 15, wherein the therapeutically effective amount of the co-crystal is about 0.01 to about 10 mg/kg body weight.

* * * * *